United States Patent
Wang et al.

(10) Patent No.: US 7,777,873 B2
(45) Date of Patent: Aug. 17, 2010

(54) REFRACTIVE INDEX SENSOR

(75) Inventors: Xiao-Ling Wang, Beijing (CN); Guo-Fan Jin, Beijing (CN); Jun Zhu, Beijing (CN)

(73) Assignees: Tsinghua University, Beijing (CN); Hon Hai Precision Industry Co., Ltd., Tu-Cheng, Taipei Hsien (TW)

( * ) Notice: Subject to any disclaimer, the term of this patent is extended or adjusted under 35 U.S.C. 154(b) by 203 days.

(21) Appl. No.: 12/187,860

(22) Filed: Aug. 7, 2008

(65) Prior Publication Data

US 2009/0116033 A1    May 7, 2009

(30) Foreign Application Priority Data

Nov. 7, 2007    (CN)    ......... 2007 1 0124285

(51) Int. Cl.
*G01N 21/41*    (2006.01)
(52) U.S. Cl. .......... 356/128; 385/125; 385/129; 385/130; 385/131
(58) Field of Classification Search .......... 356/128; 385/125, 129–131
See application file for complete search history.

(56) References Cited

U.S. PATENT DOCUMENTS

| | | | |
|---|---|---|---|
| 6,198,860 B1 * | 3/2001 | Johnson et al. | 385/28 |
| 6,697,542 B2 * | 2/2004 | Platzman et al. | 385/5 |
| 6,873,777 B2 * | 3/2005 | Bourelle | 385/129 |
| 6,879,766 B2 * | 4/2005 | Tomaru | 385/129 |
| 6,912,334 B2 * | 6/2005 | Koyama | 385/16 |
| 2005/0146778 A1 * | 7/2005 | Noda et al. | 359/321 |
| 2006/0204161 A1 * | 9/2006 | Noda et al. | 385/1 |

FOREIGN PATENT DOCUMENTS

JP    2006-234965 A    9/2006

OTHER PUBLICATIONS

E. Chow et al., Ultracompact biochemical sensor build with two-dimensional photonic crystal microcavity, Optics Letters, May 15, 2004, p. 1093-1095, vol. 29.

* cited by examiner

*Primary Examiner*—Tarifur R. Chowdhury
*Assistant Examiner*—Isiaka O Akanbi
(74) *Attorney, Agent, or Firm*—D. Austin Bonderer

(57) ABSTRACT

An exemplary refractive-index sensor includes a photonic crystal microcavity structure, a light source, and a detector. The photonic crystal microcavity structure includes a photonic crystal layer having first holes and a second hole. The first holes are arranged in a pattern of staggered parallel rows. The second hole is located at an approximate center point of the middle row of the pattern rather than a first hole. A diameter of the second hole is less than that of each of the first holes. Some of the first holes disposed at each of opposite ends of a diagonal row having the second hole are omitted to define an input waveguide and an output waveguide. The light source is adjacent to the input waveguide. The detector is adjacent to the output waveguide.

20 Claims, 4 Drawing Sheets

REFRACTIVE INDEX SENSOR

BACKGROUND

1. Field of the Invention

The invention relates to refractive-index sensors and, particularly, to a refractive-index sensor based on photonic crystals.

2. Description of Related Art

Recently, there has been interest in the use of photonic crystals to measure refractive-index change for sensing applications, because of the unique light-confinement mechanism provided by the photonic band-gap. Photonic crystals provide the potential for a high quality factor (high-Q) microcavity with small sensing area. For example, the sensing area may be 10□ μm², which requires only a very small volume (e.g., $10^{-15}$ liters) sample. These advantages make the photonic crystal an attractive candidate for use in small sample measurement. Thus, refractive-index sensors based on photonic crystals have been developed extensively.

As shown in FIG. 4, a conventional refractive-index sensor 100 based on a photonic crystal includes a substrate 102, a plurality of air holes 104, a first waveguide 108, and a second waveguide 110. The air holes 104 are etched through the substrate 102. The photonic crystal microcavity is formed by introducing one hole 106 with a diameter different from that of the air holes 104. The first waveguide 108 and the second waveguide 110 are each comprised in a side half of the substrate 102. The waveguides 108, 110 are configured to couple light in and out of the photonic crystal microcavity. The refractive-index sensor 100 is capable of detecting a change in refractive index of 0.002. Additionally, the refractive-index sensor 100 can measure a sample having a refractive index (n) from n=1.0 to n=1.5.

However, there is ongoing demand for a refractive-index sensor to provide high light transmission and improved sensitivity. A new refractive-index sensor that can meet this demand is desired.

SUMMARY

A refractive-index sensor is provided. In one embodiment, the refractive-index sensor includes a photonic crystal microcavity structure, a light source, and a detector. The photonic crystal microcavity structure includes a photonic crystal layer comprising a plurality of first holes and at least one second hole defined therein. The first holes are arranged in a regular pattern of staggered parallel rows in the photonic crystal layer. A diameter of the at least one second hole is less than a diameter of the first holes. The at least one second hole is located at an approximate center point of the middle row of the regular pattern rather than a first hole. A plurality of first holes disposed at each of opposite ends of a diagonal row having the at least one second hole are omitted to define an input waveguide and an output waveguide. The light source is disposed adjacent to the input waveguide. The detector is disposed adjacent to the output waveguide.

Other novel features and advantages of the present refractive-index sensor will become more apparent from the following detailed description of preferred and exemplary embodiments, when taken in conjunction with the accompanying drawings.

BRIEF DESCRIPTION OF THE DRAWINGS

Many aspects of the present refractive-index sensor can be better understood with reference to the following drawings.

The components in the drawings are not necessarily drawn to scale, the emphasis instead being placed upon clearly illustrating the principles of the present refractive-index sensor.

Figure 1:
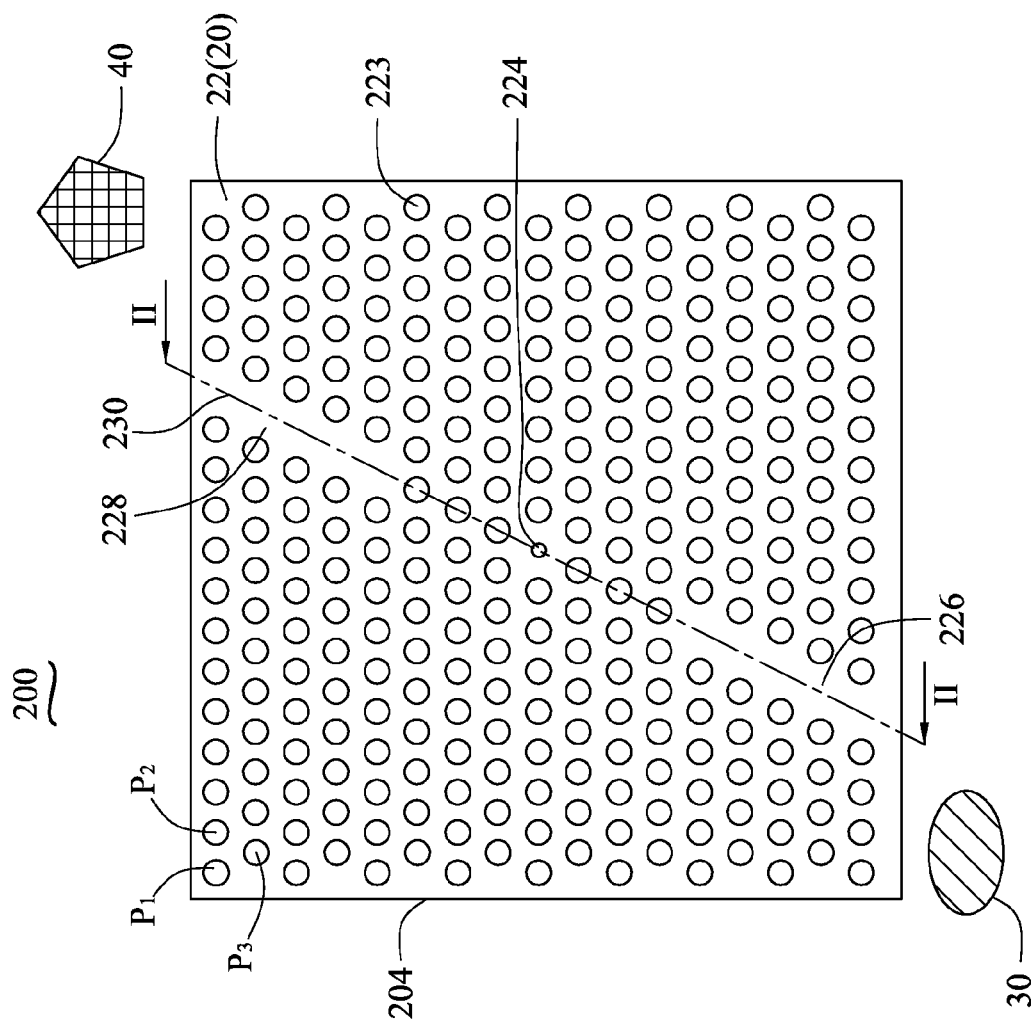
FIG. 1 is a schematic view of a refractive-index sensor, in accordance with a present embodiment.

Corresponding reference characters indicate corresponding parts throughout the several views. The exemplifications set out herein illustrate at least one preferred embodiment of the present refractive-index sensor, in one form, and such exemplifications are not to be construed as limiting the scope of the invention in any manner.

DETAILED DESCRIPTION

Reference will now be made to the drawings to describe various embodiments of the present refractive-index sensor, in detail.

Figure 2:
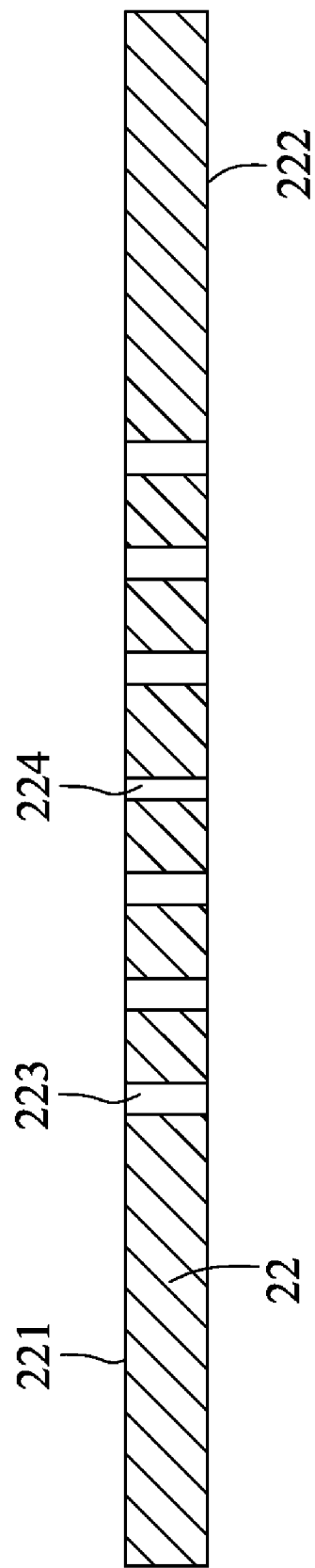
FIG. 2 is a cross-section of the refractive-index sensor of FIG. 1 taken along a line II-II thereof.

Referring to FIG. 1 and FIG. 2, a refractive-index sensor 200, according to a present embodiment, is shown. The refractive-index sensor 200 includes a photonic crystal microcavity structure 20, a light source 30, and a detector 40.

The photonic crystal microcavity structure 20 includes a photonic crystal layer 22, which has a first surface 221 and a second surface 222 at opposite sides thereof. The photonic crystal layer 22 includes a plurality of first holes 223 and at least one second hole 224 defined therein. The first holes 223 and the second hole 224 are fabricated by, for example, electron-beam lithography or reactive ion etching (RIE), and pass through the first surface 221 and the second surface 222. In the present embodiment, the first holes 223 and the second hole 224 are cylindrical. In other embodiments, the holes 223, 224 can be any of various other suitable shapes.

The photonic crystal layer 22 is made of semiconductor material, such as Si (silicon), GaAs (gallium arsenide) or GaAlAs (gallium aluminum arsenate), such semiconductor materials having refractive indices ranging from 2.7 to 3.4. Preferably, the photonic crystal layer 22 is made of GaAlAs with a refraction index of 3.32. A lattice constant of the photonic crystal layer 22 ranges from approximately 260 nm to 670 nm. Suitably, the photonic crystal layer 22 of the present embodiment is made of GaAlAs with a lattice constant of a=520 nm (nanometers). In the present embodiment, the photonic crystal layer 22 is formed in a rectangle. A thickness of the photonic crystal layer 22 ranges from approximately 0.5 a to 0.6 a, where 'a' is the lattice constant of the photonic crystal layer 22. Preferably, the thickness of the photonic crystal layer 22 is 0.6 a.

The first holes 223 are arranged in a regular pattern of staggered parallel rows in the photonic crystal layer 22. In addition, each three adjacent first holes 223 in any two adjacent rows of the first holes 223 are arranged in a triangle and are disposed corresponding to a plurality of lattice points contained in the photonic crystal layer 22. In the present embodiment, rows of the first holes 223 are parallel to each other, and a distance between adjacent rows of the first holes 223 is defined as:

$$\frac{\sqrt{3}}{2}a$$

where 'a' is the lattice constant of the photonic crystal layer 22.

In the present embodiment, the first holes 223 are arranged in an array of m rows, each of which has n holes. That is, rows of the first holes 223 are designated from top to bottom as $1^{st}$, $2^{nd}$, $3^{rd}$ ..., and $m^{th}$. The first holes 223 in each column are designated from left to right as $1^{st}$, $2^{nd}$, $3^{rd}$ ..., and $n^{th}$. Typically, each of m and n is an integer ranging from 14 to 18. The second hole 224 is located at the $j^{th}$ hole of $i^{th}$ row of the array of first holes 223, where i is more than 1 and less than m, and j is more than 1 and less than n. Preferably, i is an integer proximate to the ratio of m/2, and j is an integer proximate to the ratio of n/2. Specifically, the second hole 224 is located at an exact or approximate center point of the middle row of the pattern rather than a single first hole 223, thereby forming a resonant cavity located generally at the second hole 224. In the illustrated embodiment, the middle row of the pattern is the $9^{th}$ row. Additionally, a diameter of the second hole 224 is less than that of each of the first holes 223. The diameter of each of the first holes 223 and the diameter of the second hole 224 are chosen to provide the photonic crystal microcavity structure 20 with a desired resonant wavelength. In the present embodiment, a diameter of each of the first holes 223 is about 0.72 a, while a diameter of the second hole 224 is about 0.60 a, where 'a' is the lattice constant of the photonic crystal layer 22.

In FIG. 1, the holes 223, 224 are arranged in 17 rows. The first holes 223 in the $1^{st}$ row and the first holes 223 in the adjacent $2^{nd}$ row are disposed in an unaligned relationship. Thus, the two leftmost first holes 223 in the $1^{st}$ row, i.e., hole $P_1$ and hole $P_2$, and the leftmost first hole 223 in the $2^{nd}$ row, i.e., hole $P_3$, when connected by a line, form a triangle, preferably equilateral.

A plurality of the first holes 223 at each of opposite ends of a diagonal row of the first holes 223 having the second hole 224 are omitted. This exception in the pattern defines an input waveguide 226 and an output waveguide 228. In FIG. 1, the input waveguide 226 is formed by omitting some of the first holes 223 at one end of the diagonal row containing the second hole 224, while the output waveguide 228 is formed by omitting some of the first holes 223 at the opposite end of the diagonal row containing the second hole 224. Additionally, the input waveguide 226 and the output waveguide 228 are respectively spaced from the second hole 224 by a predetermined number of first holes 223. The number of first holes 223 between the second hole 224 and each of the input waveguide 226 and the output waveguide 228 typically ranges from approximately 2 to approximately 5. In the illustrated embodiment, the input waveguide 226 and the output waveguide 228 are each separated from the second hole 224 by three first holes 223.

The input waveguide 226, the first holes 223 disposed between the input waveguide 226 and the second hole 224, the second hole 224, and the output waveguide 228 collectively form a light guide channel 230. In the present embodiment, the light guide channel 230 intersects each of the parallel rows of the first holes 223, forming an inclined angle of about 60° at each such intersection.

The light source 30 is disposed adjacent to the input waveguide 226. The light issued from the light source 30 is directly input into the input waveguide 226 and has a wavelength within the resonant wavelength of the resonant cavity. For example, the emitted light has a wavelength ranging from 800 nm to 1600 nm. The light source 30 can be a light-emitting diode (LED) or a laser diode.

The detector 40 is disposed adjacent to the output waveguide 228. The light emitted from the light source 30 is guided through the light guide channel 230, i.e., with the light traveling through the input waveguide 226 and the output waveguide 228. The detector 40 is configured to detect the light output from the output waveguide 228. In the present embodiment, the detector 40 utilized is capable of detecting wavelengths from 800 nm to 1600 nm. Furthermore, the detector 40 can be connected to an external monitoring device so that the measurement results, e.g., output light entering the detector 40, can be monitored. In the present embodiment, the detector 40 is an optical spectrum analyzer.

During use of the refractive-index sensor 200, ambient air to be tested fills the first holes 223 and the second hole 224. When the light source 30 is active, the light emitted from the light source 30 is input to and travels through the light guide channel 230. More particularly, the light passes through the input waveguide 226 and over the resonant cavity, i.e., over the second hole 224 and the first holes 223 between the resonant cavity and the input waveguide 226 and the resonant cavity and the output waveguide 228. Finally, the light exits the output waveguide 228 to reach the detector 40. As light passes over the resonant cavity, a change in resonant wavelength is observed. As such, it is assumed that $\lambda_0$ is a wavelength corresponding to a resonant wavelength peak of the ambient air, wherein it is known that the ambient air will have a refractive index of about 1. The unknown refractive index (n) of the ambient air can be precisely obtained as follows:

$$\frac{\lambda - \lambda_0}{n-1} = 0.097\frac{\lambda_0^2}{a}$$

where $\lambda$ is a wavelength corresponding to a resonant wavelength peak of the unknown ambient air.

Figure 3:
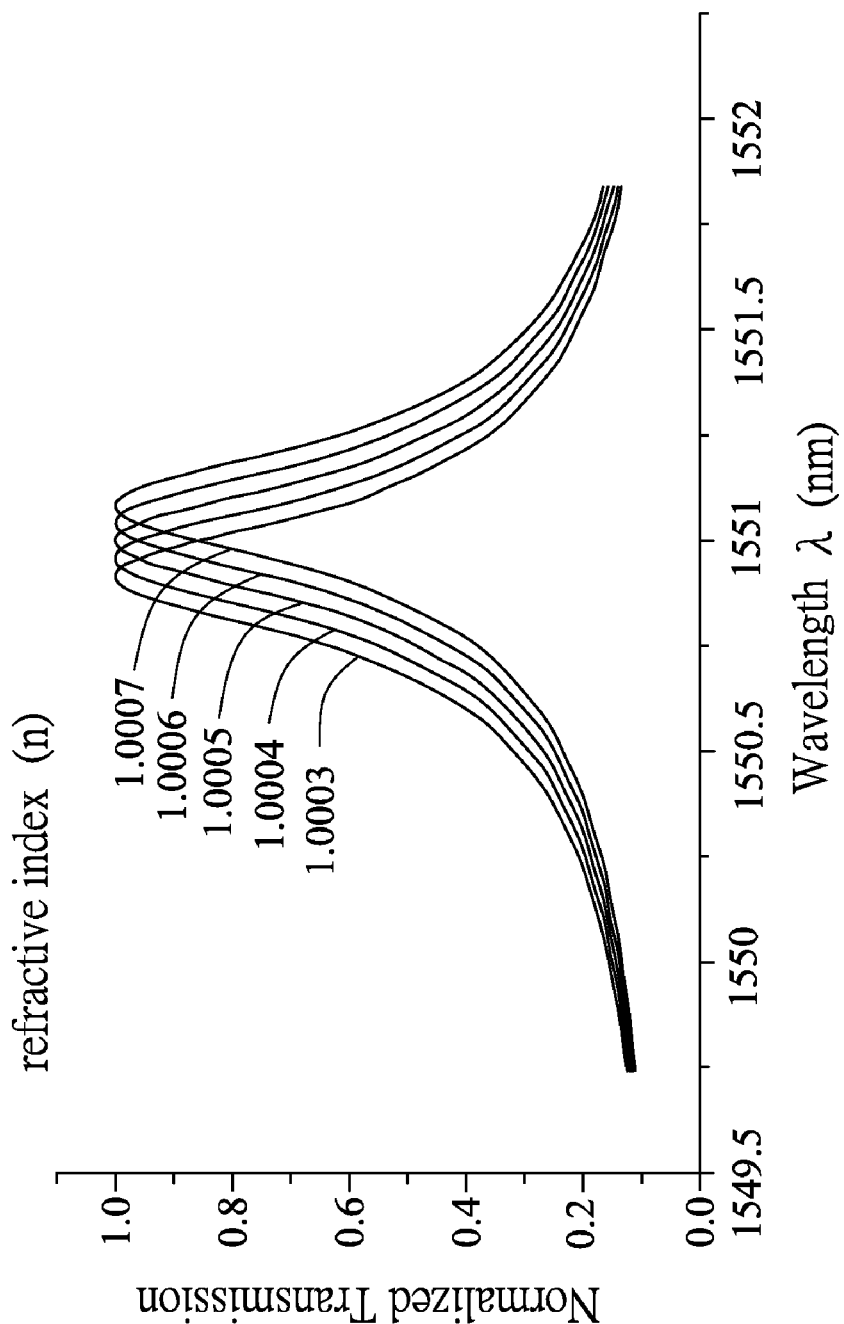
FIG. 3 is a graph showing transmission spectra of the refractive-index sensor of FIG. 1 for a particular range of refractive indices.
Figure 4:
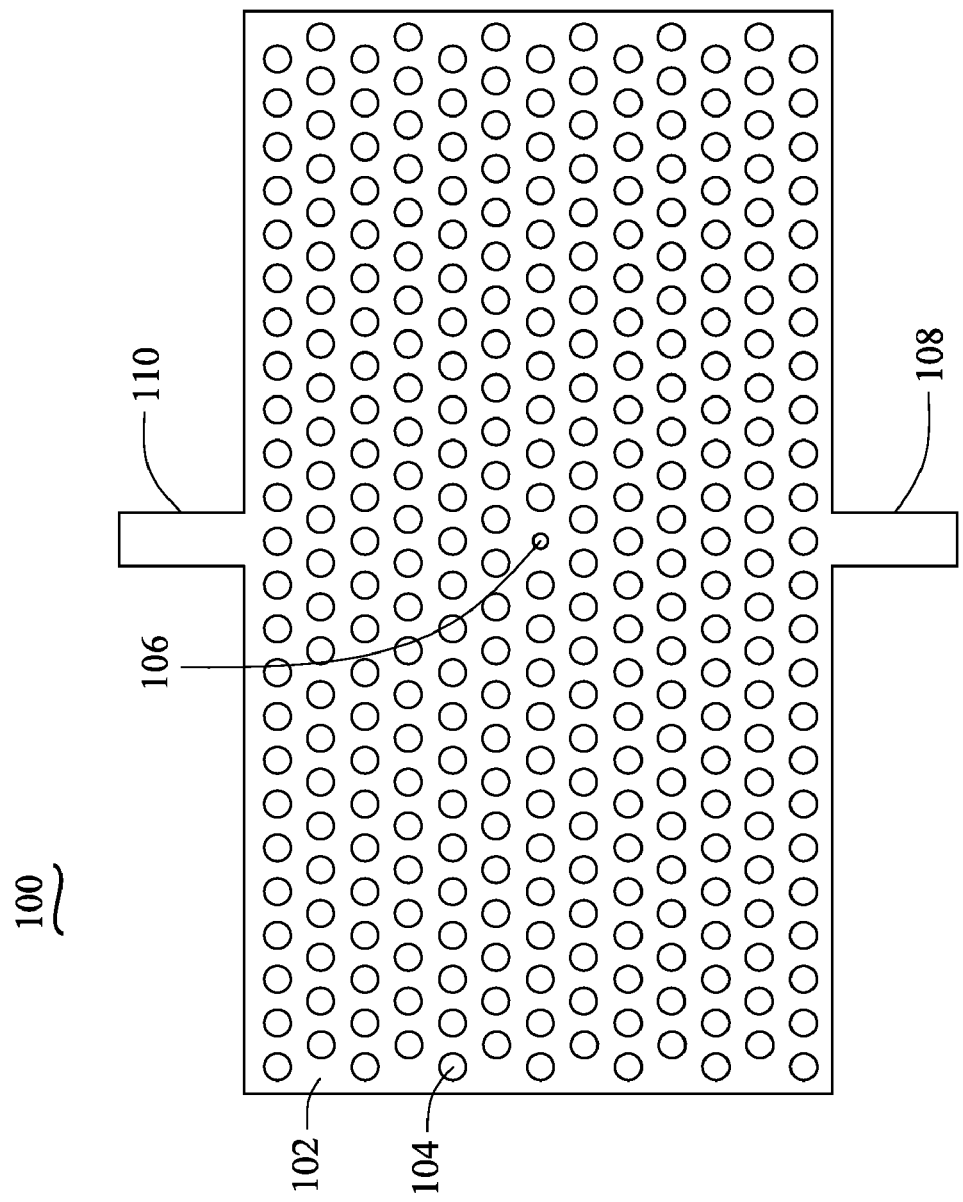
FIG. 4 is a schematic view of a conventional refractive-index sensor.

FIG. 3 is a graph of transmission spectra obtained from samples of ambient air having different refractive indices. In the present example, the refractive indices of ambient air range from 1.0003 to 1.0007 in increments of 0.0001. The light source 30 employed in the refractive-index sensor 200 of the illustrated embodiment issues light with a wavelength from 1549.5 nm to 1552.0 nm. Thus the change in resonant wavelength of a sample of ambient air having an unknown refractive index can be measured, and a corresponding refractive index of the sample can be obtained accordingly.

In conclusion, parameters such as a diameter of the first holes 223, a diameter of the second hole 224, and dispositions and configurations of the first waveguide 226 and the second waveguide 228 are chosen to improve light transmission by as much as about 67□. Consequentially, sensitivity and resolution for the refractive-index sensor 200 are improved. In particular, the refractive-index sensor 200 exhibits a sensitivity of about 443 nm/RIU (nanometers/refractive index unit). In addition, resolution of the refractive-index sensor 200 (i.e., a change in refractive index that can be detected) is about 0.0001.

Finally, it is to be understood that the embodiments described are intended to illustrate rather than limit the invention. Variations may be made to the embodiments without departing from the spirit of the invention as claimed. The embodiments illustrate the scope of the invention but do not restrict the scope of the invention.

What is claimed is:

1. A refractive-index sensor, comprising:
a photonic crystal microcavity structure comprising a photonic crystal layer having a plurality of first holes and at least one second hole defined therein, the first holes being arranged in a pattern of staggered parallel rows in the photonic crystal layer, wherein a diameter of the at least one second hole is less than that of the first holes, the at least one second hole is located at an approximate center point of the middle row of the pattern rather than a first hole, and a plurality of first holes disposed at each of opposite ends of a diagonal row of the first holes having the at least one second hole are omitted to define an input waveguide and an output waveguide;
a light source adjacent to the input waveguide; and
a detector adjacent to the output waveguide.

2. The refractive-index sensor as claimed in claim 1, wherein each three adjacent first holes in any two adjacent rows of the first holes are arranged in a triangle, and the first holes are disposed corresponding to a plurality of lattice points contained in the photonic crystal layer.

3. The refractive-index sensor as claimed in claim 1, wherein a lattice constant of the photonic crystal layer is in the range from approximately 260 nm to approximately 670 nm.

4. The refractive-index sensor as claimed in claim 3, wherein a diameter of the first holes is about 0.72 a, where 'a' is the lattice constant of the photonic crystal layer.

5. The refractive-index sensor as claimed in claim 3, wherein a diameter of the second hole is about 0.60 a, where 'a' is the lattice constant of the photonic crystal layer.

6. The refractive-index sensor as claimed in claim 3, wherein a thickness of the photonic crystal layer is in the range from approximately 0.5 a to approximately 0.6 a, where 'a' is the lattice constant of the photonic crystal layer.

7. The refractive-index sensor as claimed in claim 3, wherein a distance between adjacent rows of the first holes is about $$\frac{\sqrt{3}}{2}a,$$

where 'a' is the lattice constant of the photonic crystal layer.

8. The refractive-index sensor as claimed in claim 1, wherein an inclined angle between the diagonal row of the first holes having the at least one second hole and each of the parallel rows of first holes is about 60°.

9. The refractive-index sensor as claimed in claim 1, wherein the photonic crystal layer is made of Si, GaAs, or GaAlAs.

10. The refractive-index sensor as claimed in claim 1, wherein the photonic crystal layer is generally rectangular.

11. The refractive-index sensor as claimed in claim 1, wherein each of the input waveguide and the output waveguide is separated from the at least one second hole by a predetermined number of the first holes.

12. The refractive-index sensor as claimed in claim 11, wherein the predetermined number of first holes is from two to five.

13. The refractive-index sensor as claimed in claim 1, wherein the first holes are arranged in an array of m rows, each of which has n holes, and each of m and n ranges from 14 to 18.

14. The refractive-index sensor as claimed in claim 1, wherein at least one of the first holes and the at least one second hole are cylindrical through holes.

15. The refractive-index sensor as claimed in claim 1, wherein the light source is one of a light-emitting diode and a laser diode.

16. The refractive-index sensor as claimed in claim 1, wherein the detector is an optical spectrum analyzer.

17. A refractive-index sensor, comprising:
a photonic crystal microcavity structure comprising a photonic crystal layer having a plurality of first holes and at least one second hole defined therein, the first holes being arranged in a regular pattern of first staggered parallel rows, a diagonal row, and a regular pattern of second staggered parallel rows, the diagonal row being between the first and second staggered parallel rows, wherein the at least one second hole is located at a middle of the diagonal row of first holes, a diameter of the at least one second hole is less than that of the first holes, the number of first holes at one side of the at least one second hole in the diagonal row is no greater than one-third the number of first staggered parallel rows thereby defining an input waveguide, and the number of first holes at the other side of the at least one second hole in the diagonal row is no greater than one-third the number of second staggered parallel rows thereby defining an output waveguide;
a light source adjacent to the input waveguide; and
a detector adjacent to the output waveguide.

18. The refractive-index sensor as claimed in claim 17, wherein a diameter of the first holes is about 0.72 a, where 'a' is the lattice constant of the photonic crystal layer.

19. The refractive-index sensor as claimed in claim 17, wherein a diameter of the second hole is about 0.60 a, where 'a' is the lattice constant of the photonic crystal layer.

20. The refractive-index sensor as claimed in claim 17, wherein an inclined angle between the diagonal row of first holes having the at least one second hole and each of the first and second parallel rows of first holes is about 60°.

* * * * *